United States Patent [19]
Sims et al.

[11] Patent Number: 5,635,178
[45] Date of Patent: Jun. 3, 1997

US005635178A

[54] INHIBITION OF COMPLEMENT MEDIATED INFLAMMATORY RESPONSE USING MONOCLONAL ANTIBODIES SPECIFIC FOR A COMPONENT FORMING THE C56-9 COMPLEX WHICH INHIBIT THE PLATELET OR ENDOTHELIAL CELL ACTIVATING FUNCTION OF THE C56-9 COMPLEX

[75] Inventors: Peter J. Sims; Therese Wiedmer, both of Oklahoma City, Okla.

[73] Assignee: Oklahoma Medical Research Foundation, Oklahoma City, Okla.

[21] Appl. No.: 207,841

[22] Filed: Mar. 8, 1994

Related U.S. Application Data

[60] Continuation of Ser. No. 813,432, Dec. 24, 1991, abandoned, which is a division of Ser. No. 365,199, Jun. 12, 1989, Pat. No. 5,135,916.

[51] Int. Cl.$^6$ .................. A61K 39/395; C07K 16/18
[52] U.S. Cl. .................. 424/145.1; 530/388.25
[58] Field of Search .................. 530/388.1, 388.25, 530/45.1; 424/141.1, 156.1, 130.1; 435/240.27

[56] References Cited

U.S. PATENT DOCUMENTS

| | | |
|---|---|---|
| 4,447,415 | 5/1984 | Rock et al. |
| 4,695,460 | 9/1987 | Holme. |
| 4,916,219 | 4/1990 | Linhardt et al. |

OTHER PUBLICATIONS

Sims, P.J., "Interaction of human platelets with the complement system", *Platelet Immunobiology, Molecular and Clinical Aspects* Kunicki and George, editors, p. 354 (J.B. Lippincott Publishers, Philadelphia 1989).
Shin, et al., *Prog. Allergy* 40, 44 (1988).
Nicholson–Weller, et al., *J. Immunol.* 129, 184 (1982).
Pangburn, et al. *Proc. Natl. Acad. Sci. USA* 80, 5430 (1983).
Shin, et al., *J. Immunol.* 136(5), 1777–1782 (1986).
Zalman, et al., *Proc. Natl. Acad. Sci. USA* 83, 6975 (1986).
Schonermark, et al., *J. Immunol.* 136, 1772 (1986).
Martin, et al., *Proc. Natl. Acad. Sci. USA* 85, 213–217 (1988).
Sugita, et al., *J. Biochem.(Japan)*, 104, 633–637 1988.
Okada, et al., *Biochem. Biophys. Res. Comm.* 162, 1553 (Aug. 1989).
Davies, et al., *J. Exp. Med.* 170, 637 (Sep. 1989).
Rollins, et al., *Complement and Inflammation* 6, 394 (1989).
Wiedmer and Sims, *J. Biol. Chem.* 260, 8014–8019 (1985).
Wiedmer, et al., *J. Biol. Chem.* 262, 13674–13681 (1987).
Sims, et al., *J. Biol. Chem.* 263, 18205–18212 (1988).
Okada, et al., *Int. Immunol.* 1(2), 205–208 (1989).
Holguin, et al., *J. Clin. Invest.* 84, 7–17 (Jul. 1989).
Groux, et al., *J. Immunol.* 142(9), 3013–3020 (May 1989).
Stefanova, et al., *Molecular Immunology* 26(2), 153–161 (1989).
Sims, et al., *J. Biol. Chem.* 264(29) 17049–17057 (1989).
Sims, et al., "Regulatory Control of complement on Blood Platelets: Modulation of Platelet Procoagulant Responses by a membrane inhibitor of the C5b–9" *J. Biol. Chem.* (1989) 19228–19235.
Hamilton, et al., "Complement Proteins C5b–9 Increase Endothlial Prothrombinase Activity" *Circulation* (1989) 11315.
Wiedmer, et al., "The Role of Calcium and Calpain in Complement–Induced Vesiculation of the Platelet Plasma Membrane and in the Exposure of the Platelet Factor Va Receptor", *Biochemistry* 29:623–632 1990.
Nicholsaon–Weller et al (1985) *Blood* 65(5), 1237–1244.
Coding "Monoclonalantibodies," Academic Press, Orlando, pp. 56–93 and 118–125.
Thorpe (1993) *Trends in Biotech.* 11:40–42.
Simpson et al (1988) *J. Clin. Invest.* 81:624–629.
Harlow et al (Eds) "Antibodies A Laboratory Manual" (1988) Cold Spring Harbor Laboratory, Cold Spring Harbor Press, pp. 98 & 150–169, 207–211, & 216–217.
Gregonadis et al (1993) *Trends in Biotech.* 11:440–442.
Kohler et al (1975) *Nature* 256:495–497.
Wurzner et al (1991) *Complement Inflamm* 8:328–340.
Kabat et al (Eds) "Experimental Immunochemistry," Charles C. Thomas, Springfield, Ill. pp. 135–139, (1961).
Coligan et al (Eds.) "Current Protocods in Immunology" (1992), Green Publishing Associates and Wiley–Interscience, New York, pp. 2.5.1–2.5.17.

Hatton et al (1989, May 25) J. Biol. Chem. 264(15):9053–9060.
Hugo et al (1987) J. Immunol. Methods 99:243–251.
Gyongyossy-Issa et al (1993) Blood 82 (0,Suppl.):336a.

*Primary Examiner*—Paula K. Hutzell
*Attorney, Agent, or Firm*—Arnall Golden & Gergory

[57] ABSTRACT

Compositions and methods for use thereof relating to monoclonal antibodies, and fragments thereof, having inhibitory activity towards the cell-activating function of the complement C5b-9 complex. The compositions can be used in vitro to inhibit C5b-9 related stimulatory responses of platelets and/or endothelial cells, thereby preventing C5b-9-initiated cell necrosis or stimulated secretion of proteolytic enzymes and the exposure of the procoagulant membrane receptors during collection and in vitro storage. Further, disease states can be treated by administering to platelets and/or endothelial cells in vivo an effective amount of a monoclonal antibody, or fragment thereof, which has inhibitory activity towards the cell-activating function of the C5b-9 complex, in a pharmaceutically acceptable carrier.

5 Claims, 5 Drawing Sheets

INHIBITION OF COMPLEMENT MEDIATED INFLAMMATORY RESPONSE USING MONOCLONAL ANTIBODIES SPECIFIC FOR A COMPONENT FORMING THE C56-9 COMPLEX WHICH INHIBIT THE PLATELET OR ENDOTHELIAL CELL ACTIVATING FUNCTION OF THE C56-9 COMPLEX

The U.S. Government has rights in this invention by virtue of certain government grants.

This is a continuation of U.S. Ser. No. 07/813,432, filed Dec. 24, 1991 (abandoned), which is a divisional of U.S. Ser. No. 07/365,199 filed Jun. 12, 1989, issued on Aug. 4, 1992 as U.S. Pat. No. 5,135,916.

BACKGROUND OF THE INVENTION

The present invention generally relates to compositions, and methods for use thereof, effective in regulating inflammatory platelet and endothelial stimulatory and coagulopathic responses by modulating the activity of the C5b-9 complex of the human plasma complement system.

The complement system is a complex interaction of plasma proteins and membrane cofactors which act in a multi-step, multi-protein cascade sequence in conjunction with other immunological systems of the body to provide immunity from intrusion of foreign cells. Complement proteins represent up to about 10% of globulins in normal serum of man and other vertebrates.

The classic complement pathway involves an initial antibody recognition of, and binding to, an antigenic site (SA) on a target cell. This surface bound antibody subsequently reacts with the first component of complement, C1q, forming a C1-antibody complex with Ca++, C1r, and C1s which is proteolytically active. C1s cleaves C2 and C4 into active components, C2a and C4a. The C4b,2a complex is an active protease called C3 convertase, and acts to cleave C3 into C3a and C3b. C3b forms a complex with C4b,2a to produce C4b,2a,3b, which cleaves C5 into C5a and C5b. C5b combines with C6. The C5b,6 complex combines with C7 to form the ternary complex C5b,6,7. The C5b,6,7 complex binds C8 at the surface of the cell, which may develop functional membrane lesions and undergo slow lysis. Upon binding of C9 to the C8 molecules in the C5b,6,7,8 complex, lysis of bacteria and other foreign cells is rapidly accelerated.

Recently, the C5b-9 proteins of the human plasma complement system have been implicated in non-lytic stimulatory responses from certain human vascular and blood cells. The capacity of C5b-9 to modify membrane permeability and to selectively alter ion conductance is thought to elicit these non-lytic responses from human cells. In the case of human blood platelets and vascular endothelium, assembly of the C5b-9 complex initiates a transient and reversible depolarization of the plasma membrane potential, a rise in cytosolic Ca2+, metabolic conversion of arachidonate to thromboxane or prostacyclin, and the activation of intracellular protein kinases. In addition, human platelets exposed to C5b-9 undergo shape changes, secretory fusion of intracellular storage granules with plasma membrane, and the vesiculation of membrane components from the cell surface. Human endothelial cells exposed to the human C5b-9 proteins secrete high molecular weight multimers of the platelet adhesion protein, von Willibrand Factor (vWF), and the intracellular granule membrane protein, GMP140, is translocated from the Weible-Palade body to the endothelial surface. High molecular weight multimers of vWF have been implicated in the pathogenesis of vaso-occlusive platelet adherence to endothelium and cell surface GMP140 has been implicated in the adherence of inflammatory leukocytes to endothelium.

These effects of complement proteins C5b-9 on platelet and endothelial cells alter the normal regulation of the enzymes of the plasma coagulation system at these cell surfaces. For example, the generation of platelet membrane microparticles by vesiculation results in the exposure of membrane binding sites for coagulation factor Va. Binding of factor Va to these membrane microparticle sites initiates assembly of the prothrombinase enzyme complex. This complex in turn accelerates coagulation factor Xa activation of prothrombin to thrombin which promotes plasma clotting. Similarly, C5b-9 binding to the endothelial cell results in the exposure of plasma membrane receptors for the prothrombinase complex, thereby accelerating the generation of thrombin from prothrombin at the endothelial surface.

This interaction between components of the complement and coagulation systems at the surface of blood platelets and endothelium can generate inflammatory and chemotactic peptides at sites of vascular thrombus formation and may contribute to the altered hemostasis associated with immune disease states. In addition, immune reactions affecting blood platelets and endothelium can lead to platelet aggregation, the secretion of proteolytic enzymes and vasoactive amines from platelet storage granules, and increase adherence of platelets and leukocytes to the endothelial lining of blood vessels.

It has been demonstrated that membrane-uptake of C3b and C5b-9 proteins can occur spontaneously during incubation of platelets in citrated plasma. Complement activation can also occur during blood collection as a result of exposure to plastic surfaces supporting the C3-convertase reaction. While the implications of complement activation during blood collection and in vitro storage for transfusion have not been directly addressed it is, nevertheless, known that plasma levels of coagulation factors V and VIII rapidly decline in stored platelet concentrates at a rate considerably faster than their decay in cell-free plasma, suggesting consumptive loss. Further, platelet collection and storage is associated with an increase in vesicular plasma membrane microparticles, a product of C5b-9 initiated platelet secretion. These physiological and enzymatic changes greatly reduce the potential shelf life of stored platelets, particularly platelet-rich plasma concentrates used for transfusions, which is generally only 72 hours at best. Furthermore, this interaction of activated C5b-9, platelets, and coagulation factors in stored platelet concentrates will adversely affect the hemostatic effectiveness of these units when infused.

In vitro human organ and tissue storage and survival of the transplanted graft is also adversely affected by the spontaneous activation of the complement system, resulting in membrane insertion of the C5b-9 proteins into vascular endothelium. Activation of C5 to C5a and C5b has been shown to be catalyzed by plastics and other synthetic membranes required to maintain perfusion of vascular beds during in vitro tissue and organ storage. In addition, membrane deposition of C5b-9 in vivo has been implicated in the acute rejection of transplanted tissue due to immune activation of the recipient's plasma complement system against the endothelial cells within the donor's organ.

Platelet and endothelial cell activation by C5b-9 also has ramifications in autoimmune disorders and other disease states. The importance of spontaneous complement activation and the resulting exposure of platelets and endothelium to activated C5b-9 to the evolution of vaso-occlusive disease is underscored by consideration that a) leukocyte infiltration of the subendothelium, which is known to occur in regions of atheromatous degeneration and suggests localized generation of C5a at the vessel wall, is potentially catalyzed by adherent platelets and b) local intravascular complement activation resulting in membrane deposition of C5b-9 complexes accompanies coronary vessel occlusion and may affect the ultimate extent of myocardial damage associated with infarction.

It is therefore an object of the present invention to provide a means and method for the modulation and inhibition of complement C5b-9 mediated platelet and endothelial cell activation in vivo and in vitro.

It is a further object of the present invention to provide a means and method for increasing the survival and therapeutic efficacy of platelets and tissues or organs collected and stored in vitro.

It is a still further object of the present invention to provide protection to transplanted organs or tissue and transfused blood cells by prior in vitro incorporation of a membrane inhibitor of the C5b-9 complex.

It is another object of the present invention to provide methods of treatment for selected autoimmune disorders and other disease states.

SUMMARY OF THE INVENTION

A composition and methods for use thereof relating to polypeptides having the ability to act as an inhibitor of complement C5b-9 complex activity. The compositions contain an 18 kDa protein found on the surface of human erythrocytes, a 37 kDa protein found on the surface of human platelets, a 37 kDa protein found on the surface of human endothelial cells, active derivatives or fragments thereof which act to inhibit the activity of C5b-9, anti-idiotypic antibodies mimicking the action of the inhibitor proteins or antibodies against C7 or C9 which block the formation of the C5b-9 complex.

The compositions can be used in vitro to inhibit C5b-9 related stimulatory responses of platelets and vascular endothelium of perfused organs and tissues, thereby preventing the C5b-9 initiated cell necrosis or stimulated secretion of proteolytic enzymes and the exposure of the procoagulant membrane receptors during collection and in vitro storage. In one variation of this embodiment, the vascular endothelium of organs and tissues to be transplanted are treated with these compositions to protect these cells from complement activation after transplantation. In another embodiment, immune disease states are treated by administering an effective amount of a C5b-9 inhibitor to suppress C5b-9 mediated platelet activation in vivo.

Also disclosed are methods for the production of isolated polypeptides that are able to suppress complement C5b-9 mediated platelet and endothelial cell activation.

BRIEF DESCRIPTION OF THE DRAWINGS

FIG. 5A shows the level of factor Va binding site measured using the FITC-labeled monoclonal antibody V237, directed against the factor Va light chain, measured in the presence of 2 µg/ml of the ligand. FIG. 5B represents measured prothrombinase activity (thrombin units/min×$10^8$ platelets). Both FIG. 5A and 5B compare using control C5b-9 (hatched bars) or treated (100 µg/ml α-P18) (solid bars) platelets. Data for complement free controls are also shown.

Figure 1:
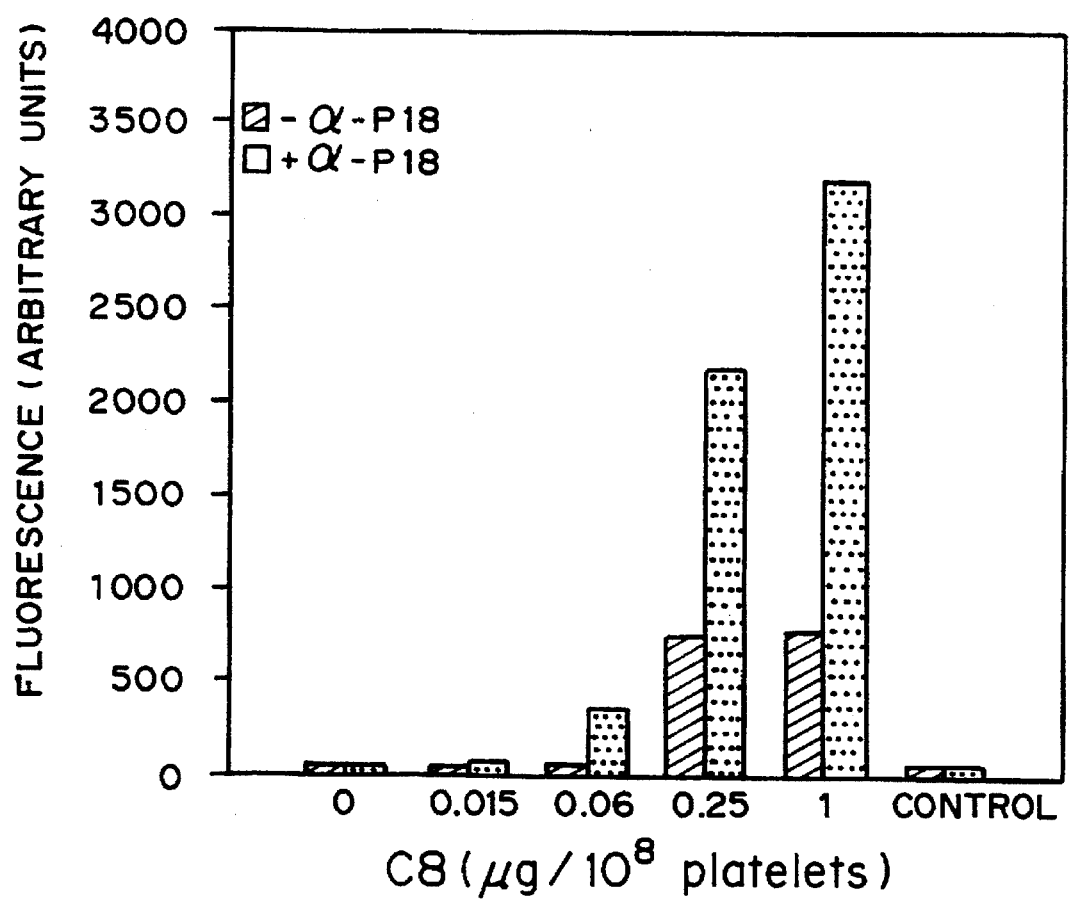
FIG. 1 shows the effect of α-P18 on C9 incorporation into platelet membrane C5b-9 complexes. Platelets were incubated with 100 µg α-P18/ml (solid bars) or 0 µg α-P18/ml (hatched bars) and the amount of FITC-labeled anti-C9 neo-epitope antibody that bound to the platelets in the presence of various concentrations of C8 (0, 0.015, 0.06, 0.25, and 1 µg C8/$10^8$ platelets) was measured by fluorescence.

DETAILED DESCRIPTION OF THE INVENTION 37 kDa platelet and endothelial plasma membrane inhibitors of the C5b-9 complex which normally serve to attenuate the procoagulant responses of blood platelets and endothelium exposed to activated complement proteins have been discovered by cross-reaction with a monospecific antibody (α-P18) raised against an 18 kDa erythrocyte membrane inhibitor of C5b-9 which was identified by Sugita, et al., *J. Biochem.* (Japan), 104:633–637, (1988). The existence of these proteins and the studies detailed below indicate that a deletion or inactivation of these cell surface components would increase the risk of vascular thrombosis and lead to a decreased storage time for platelets and platelet rich plasma (PRP), and perfused organs and transplanted tissue. Accordingly, the survival and hemostatic efficacy of platelets, and the survival of organs and tissue for transplant, which are collected and stored in vitro, can be increased by addition of the C5b-9 inhibitor to the storage buffer or perfusate. Autoimmune disorders and other disease states that involve C5b-9 mediated platelet activation, including lupus, rheumatoid arthritis, and other types of immunovasculitis, can also be treated by the intravascular administration an effective amount of the inhibitor to suppress C5b-9 activity, or a composition containing a polypeptide C5b-9 inhibitor to a patient requiring such treatment. Similar uses of the inhibitor may be applicable for cell culture in human blood derived culture media.

The conclusions as to the mechanisms by which the platelet bound inhibitor inhibits the C5b-9 inflammatory response is based on the following. Addition of the purified 18 kDa protein, isolated from human erythrocyte membranes, to other blood cells or endothelium serves to protect these cells from both the cytolytic and cell-stimulatory effects of the C5b-9 complement proteins. The function of this 18 kDa C5b-9 inhibitory protein, when bound to platelet and endothelial cell surfaces, was also probed by raising a neutralizing (blocking) antibody (α-P18) that abrogates the C5b-9 inhibitory function of the purified molecule in vitro as well as the endogenous C5b-9 inhibitory factors, which may include the 18 kDa and 37 kDa proteins. When bound to the platelet surface, the FAB of α-P18 increases C9 activation by membrane C5b-8, as monitored by exposure of a complex-dependent C9 neo-epitope. Although α-P18 causes little increase in the cytolysis of platelets treated with C5b-9 (as determined from the total release of lactate dehydrogenase of less than 5%), it markedly increases the cell stimulatory responses induced by these complement proteins, including secretion from platelet alpha and dense granules, conformational activation of cell surface GPIIb-IIIa, release of membrane microparticles from the platelet surface, and exposure of new membrane binding sites for components of the prothrombinase enzyme complex. Prior incubation of C5b67 platelets with 100 µg/ml α-P18 (Fab) lowers by approximately 10-fold the half-maximal concentration of C8 required to elicit each of these responses in the presence of excess C9. Incubation with α-P18 (Fab) alone does not activate platelets, nor does incubation with this antibody potentiate the stimulatory responses of platelets exposed to other agonists.

As used herein in the compositions and methods for the prolongation of platelet and organ survival and enhancement of therapeutic efficacy or suppression of complement mediated disorders, "C5b-9 inactivator" refers to the 37 kDa protein from platelets, the corresponding 37 kDa protein on endothelial cells, the 18 kDa protein on erythrocyte membranes, peptide fragments thereof having C5b-9 inhibitory activity, and preferably containing a membrane binding domain, whether isolated from naturally produced materials or recombinantly engineered sequences, monoclonal antibodies to C7 that block membrane binding of the C5b-9, monoclonal antibodies to C9 that block C9 polymerization and insertion into the membrane, monoclonal antibodies that blocks C9 binding to C5b-9, and anti-idiotypic antibodies which inhibit the function of the cell surface molecules in inhibiting C5b-9 activity, especially the Fab fragments of monoclonal antibodies having this activity. All molecular weights are determined by SDS-PAGE under non-reducing conditions. The 37 kDa and 18 kDa proteins are species specific, i.e., only inhibitor proteins of human origin will inhibit human C5b-9.

These studies are described in more detail below.

Experimental Procedures

Materials:

Bovine serum albumin (globulin and fatty acid free), prostaglandin E1, apyrase, phorbol myristate acetate (PMA) and N-hydroxysuccinimide biotin ester were obtained from Sigma Chemical Co., St. Louis, Mo.; (p-amidino-phenyl) methanesulfonyl fluoride (pAPMSF) was from Med Cal; fluorescein-5-isothiocyanate (isomer I) was from Molecular Probes; phycoerythrin-streptavidin conjugate was from Southern Biotechnology Associates (Birmingham, Ala.) and Spectrozyme TH was from American Diagnostica (Greenwich, Conn.). IODO-GEN was from Pierce Chemical Co.; $Na^{125}I$ from ICN Biochemicals, and $[^{14}C]$serotonin was from Du Pont-New England Nuclear. Human complement proteins C5b6, C7, C8 and C9 were purified and analyzed for functional activity according to methods previously described by Wiedmer and Sims, *J. Biol. Chem.* 260, 8014–8019 (1985). Bovine factors Va, Xa, prothrombin, thrombin, and the light chain of factor Va were gifts from Dr. Charles T. Esmon (Oklahoma Medical Research Foundation). All other chemicals were of reagent or analytical grade.

Solutions:

Solution I: 145 mM NaCl, 4 mM KCl, 0.5 mM Mg $Cl_2$, 0.5 mM sodium phosphate, 0.1% (w/v) glucose, 0.1% bovine serum albumin, 5 mM PIPES, pH 6.8.

Solution II: 137 mM NaCl, 4 mM KCl, 0.5 mM $MgCl_2$ 0.5 mM sodium phosphate, 0.1% glucose (w/v), 0.12% bovine serum albumin, 20 mM HEPES, pH 7.4.

Erythrocyte Membrane Protein Inhibitory for C5b-9

The 18 kDa human erythrocyte protein inhibitory for C5b-9 lysis was isolated by modification of methods described by Sugita, et al. (1988). Additional purification was obtained by Mono-Q™ FPLC (Pharmacia). When incorporated into erythrocytes, this protein inhibited the hemolytic activity of the purified human C5b-9 proteins, due to inhibition of C9 activation by membrane C5b-8. When subjected to 12% polyacrylamide SDS-PAGE (non-reducing), all of the C5b-9-inhibitory activity of this protein was found to elute from a gel slice corresponding to a single protein band at 18 kDa molecular weight.

In addition to classical protein purification using column chromatography, an example of which is discussed above, polypeptides having inhibitory activity can also be affinity purified using inhibitor specific antibodies. Antibodies, such as α-P18 disclosed below, which bind the C5b-9 inhibitor polypeptide, are immobilized on chromatographic matrix material by techniques well known to those skilled in the art.

Erythrocytes or platelets containing the C5b-9 inhibitor protein on their surface are isolated from whole blood by centrifugation and detergent solubilized. The resultant solubilized crude extract is then mixed with matrix immobilized antibody either in a batch process or chromatographically. The immobilized antibodies specifically bind C5b-9 inhibitor polypeptides while the remainder of the crude extract is easily removed by washing. The purified inhibitor is then eluted and collected.

Alternatively, polypeptides having the ability to inhibit C5b-9 mediated procoagulant responses are produced recombinantly using methods and techniques well known to those in the art. For example, human DNA is isolated and digested with restriction enzymes to create fragments of appropriate size and with appropriate cohesive ends to be ligated into any of the known and commercially available (e.g. Promega's lambda gt11 vector system) expression vectors. Alternatively, the isolated DNA is sheared and the appropriate linkers are ligated onto the resulting fragments which are then inserted into the expression vector of choice.

Vectors containing human DNA fragments are next transformed into the appropriate bacterial strain, normally a strain of *E. coli* that is included in the expression vector kit, to generate the DNA gene bank or library. Plating out the vector containing bacteria of the library on appropriate media results in expression of the inserted human DNA fragment. The colonies are screened for the presence of DNA encoding and expressing the C5b-9 inhibitory polypeptide using specific antibodies such as α-P18 disclosed below. Positive colonies are isolated and used for the large scale expression of recombinantly produced inhibitory protein.

In this fashion intact inhibitory protein can be made recombinantly as well as modified polypeptides and functional fragments and derivatives thereof. Functional polypeptides possessing the ability to inhibit C5b-9 can be produced by any of the above discussed method or by other techniques commonly known to those of ordinary skill in the art. These isolated and purified polypeptides can be further mixed with pharmaceutically acceptable carriers to form compositions for use in prolonging cell storage or in treatment of immune disorders or diseases.

Antibodies:

Murine monoclonal antibody S12, specific for the platelet α-granule membrane glycoprotein, GMP-140, was a gift from Dr. Roger P. McEver (Oklahoma Medical Research Foundation, Oklahoma City). Murine monoclonal antibody AP1, specific for membrane glycoprotein, GP Ib, was from Dr. Thomas J. Kunicki (Blood Center of Southeastern Wisconsin, Milwaukee). Murine monoclonal PACl, specific for the activated conformation of the GP IIb-IIIa complex, was from Dr. Sanford J. Shattil (University of Pennsylvania, Philadelphia). Murine monoclonal antibody MAC, specific for a neo-epitope in C9 exposed upon its incorporation into membrane C5b-9 or SC5b-9, was from Dr. John Tamerius (Cytotech Corp.). Murine monoclonal antibody V237 recognizes an epitope in the light chain of factor Va (human or bovine) and binds to both factor V and factor Va. Murine monoclonal antibodies against the human C5b-9 proteins were raised by immunization against the purified human proteins and then screened for inhibitory activity towards the cytolytic or cell activating function of the C5b-9 complex. These monoclonal antibodies, or their Fab fragments, mimic the inhibitory function of the plasma membrane C5b-9 inhibitor in that they raise the threshold amount of activated C5b-9 required to achieve either red cell lysis or platelet and endothelial cell activation.

Monospecific rabbit antibody against the purified human erythrocyte 18 kDa protein (α-P18) was raised by repeated injection of the purified and isolated C5b-9 inhibitory polypeptide antigen isolated by the modification of the method of Sugita, et al. (1988). Immunized rabbit blood was collected and the IgG fraction was isolated by absorption to immobilized staph protein A, followed by gel permeation chromatography on Sephadex G200 (Pharmacia). Western blotting against detergent solubilized extracts of human erythrocyte membrane proteins demonstrated that this antibody was monospecific for a single protein of 18 kDa (non-reduced). Reactivity of this antibody was lost upon disulfide reduction of the antigen.

Fab fragments of IgG were prepared by 2 h digestion at 37° C. with immobilized papain (Pierce). The resulting Fab fragments were purified to homogeneity by absorption against immobilized staph protein A and gel permeation chromatograph (Sephadex™ G150; Pharmacia).

Fluorescence Labeling:

For flow cytometry, all antibodies were conjugated with FITC, except antibody AP1, which was conjugated with N-hydroxysuccinimide biotin ester as described previously. Dye-to-protein ratios ranged from 3-to-5.

Protein Concentrations:

Concentrations of unlabeled proteins were estimated assuming the following extinction coefficients ($E^{1\%}{}_{280}$): murine IgG (15), factor Va (15.1), factor Va light chain (18.7), factor Xa (12.4), prothrombin (15.5), C5b6 (10), C7 (9.9), C8 (15.1), and C9 (9.6). The concentrations of FITC-labeled proteins were determined by dye binding assay (BioRad), using the respective unlabeled protein as standard. FITC concentration was determined assuming a molar extinction (492 nm) of 68,000.

Effect of α-p18 on Platelet Activity by C5b-9

Gel-filtered human platelets were prepared and collected into Solution I at 1–2×$10^9$ ml as described by Wiedmer and Sims, *J. Biol. Chem.* 260, 8014-8019 (1985) or Wiedmer, et al., *J. Biol. Chem.* 262, 13674–13681 (1986). To assemble membrane-bound C5b67 complexes, gel-filtered platelets ($10^9$/ml) were incubated for 5 min at 37° C. with C5b6 (15 μg/$10^8$ platelets). The C5b67 platelets were then incubated with the Fab fragments of a α-P18 (0 to 125 μg/ml) for 10 min at room temperature. After dilution to $10^8$ platelets/ml in Solution II containing 2.5 mM Ca $Cl_2$, C8 (0 to 1 μg per $10^8$ cells) and C9 (0 or 4 μg per $10^8$ cells) were added, and the cells incubated at 37° C. without stirring for 10 min. In all studies, comparison was made to identical matched-pair controls (platelets incubated in the absence of the C5b-9 proteins). In certain experiments, comparison was also made to gel-filtered platelets stimulated by incubation (10 min at 37° C. without stirring) with PMA (0–0.1 μM) or thrombin (0.–0.5 U/ml).

Preparation of Platelets for Flow Cytometry

5×$10^8$ C5b-9 treated or control platelets were incubated in the dark in a total volume of 60 μl for 10 min at 23° C. in the presence of biotin-AP1 (1 μg/ml) and one or more of the following fluorescein-conjugated antibodies: FITC-α-P18 (Fab; 50 μg/ml), FITC-MAC (30 μg/ml), FITC-S12 (10 μg/ml), or FITC-V237 (20 μg/ml). To measure membrane binding sites for factor Va, cells were first incubated for 10 min at 23° C. with factor Va light chain (2 μg/ml) before addition of FITC-V237. Following incubation with the labeled antibodies, phycoerythrinstreptavidin was added (5 μl of a 1:20 dilution), and the cells were incubated an additional 10 min. Then 0.5 ml aliquots of Solution II were added and the samples analyzed flow cytometry. All analyses were complete within 30 min.

Flow Cytometry:

Platelets were analyzed in a Becton Dickinson FACSCAN flow cytometer formatted for two-color analysis. The light scatter and fluorescence channels were set at logarithmic gain. In order to resolve platelet-derived microparticles from background light scatter, acquisition was gated so as to include only those particles distinctly positive for biotin-AP1 (detected as phycoerythrin Fluorescence), using a fluorescence lower-limit threshold on the 585 nm channel that excluded background scatter. Thus, only those cells and microparticles expressing the platelet-specific membrane glycoprotein, GP Ib, were included for analysis. Ten thousand phycoerythrin-positive particles from each sample were analyzed for forward and right angle light scatter and for FITC and phycoerythrin fluorescence intensities. To measure FITC-α-P18 binding to erythrocytes, the threshold for acquisition was set on forward scatter. All fluorescence data were corrected for cell or microparticle autofluorescence (generally, ≦2 arbitrary fluorescence units per particle). Where indicated, correction for non-specific binding was made by incubation of cells with FITC-labeled antibody in the presence of a 20-fold excess the unlabeled antibody (IgG or Fab).

Secretion and Cell Lysis Assays:

Dense granule secretion was measured by the release of [$^{14}$C]serotonin. Alpha granule secretion was monitored by the surface expression of GMP-140, detected by the binding of FITC-labeled monoclonal antibody S12. Cell lysis was monitored by release of cytoplasmic lactic acid dehydrogenase.

Prothrombinase Assay:

Platelet prothrombinase activity was measured by modification of methods previously described, using the chromogenic substrate Spectrozyme TH, by Wiedmer, et al., *Blood* 68, 875–880 (1986). After activation, platelets were diluted to a final concentration of $5 \times 10^6$ per ml in Solution II containing 1% albumin, 2.5 mM $CaCl_2$, 2 nM factor Va, and 2.7 µM prothrombin, and incubated at 37° C. Prothrombin conversion was initiated by addition of factor Xa to a final concentration of 2 nM. The reaction was stopped at 0, 30, and 60 seconds by transfer of 1 vol of sample into 9 vol of ice cold buffer containing 1% albumin and 10 mM EDTA, and thrombin assayed as described by Wiedmer, et al., (1986).

Studies relating to the C5b-9 mediated activation of human cultured umbilical vein endothelial cells were performed as described by R. Hattori, et al., *J. Biol. Chem.* 264, 7768–7771 (1989).

Results:

α-P18 Binds Specifically to the Platelet plasma Membrane and Increases the Incorporation of Activated C9 into Membrane c5b-9

The hemolytic activity of the terminal complement proteins appears to be regulated by two distinct proteins expressed on the surface of human erythrocytes: "homologous restriction factor" (also referred to as "C8-binding protein") with an apparent molecular weight of 64 kDa, and an 18 kDa protein that does not exhibit C8-binding activity. Both of these membrane proteins have been shown to inhibit the cytolytic activity of the human terminal complement proteins, apparently by affecting the interaction of C9 with membrane bound C5b-8. Evidence has been presented that homologous restriction factor is normally bound to the cell surface by linkage to membrane phosphatidylinositol, and that this protein is deleted from the affected blood cells obtained from patients with the disorder Paroxysmal Nocturnal Hemoglobinuria (PNH).

In order to determine whether the 18 kDa component of the erythrocyte membrane also plays a role in regulating the C5b-9 complex on the platelet surface, an antibody (α-P18) that binds to the 18 kDa erythrocyte protein and abrogates its C5b-9-inhibitory function was produced. In addition to binding erythrocytes, this antibody was found to bind specifically to platelets, as demonstrated by the results in Table I.

TABLE I

Binding of α-P18 to Human Platelets and Red Blood Cells[1]

| | ERYTHROCYTES | PLATELETS |
|---|---|---|
| FITC-Fab | 86,100 ± 300 | 22,800 ± 200 |
| FITc-IgG | 415,100 ± 600 | 103,000 ± 600 |

(mean ± s.d., n = 3)

[1]Cell binding of FITC-labeled α-P18 (IgG or Fab) was measured and corrected for non-specific binding as described in Materials and Methods. Data are expressed as fluorescence (arbitrary units) per $10^4$ cells.

When bound to red cells, α-P18, or its Fab fragment, neutralized the C9-inhibitory activity of the 18 kDa membrane protein, and thereby increased the lytic susceptibility of the cells to purified C5b-9. Conversely, addition of the purified 18 kDa protein to blood cell suspensions acted to inhibit cell lysis or cell activation by the C5b-9 proteins. To test the effect of this antibody on platelets, gel-filtered human platelets were first exposed to the C5b67 proteins, and then incubated with α-P18 (Fab fragments) before addition of C8 plus C9.

C5b67 platelets were incubated for 15 min at 23° C. with either 0 (hatched bars) or 100 µg/ml (solid bars) α-P18 (Fab) before addition of C9 (4 µg per $10^8$ cells) plus varying amounts of C8. After an additional 10 min incubation at 37° C., samples were stained with FITC-labeled monoclonal antibody against C9 neo-epitope (FITC-MAC) and processed for flow cytometry. The results are shown in FIG. 1. The ordinate denotes total membrane-associated fluorescence (arbitrary units), corrected for non-specific binding of FITC-MAC. Data for C9-free controls are also shown.

As shown by these data, incubation with α-P18 increased the amount of activated C9 incorporated into plasma membrane C5b-9 complexes, suggesting that this antibody also neutralizes a c5b-9 regulatory function of the platelet membrane. In these studies, the activated form of C9 was detected by use of a fluorescently-labeled monoclonal antibody (FITC-MAC) that recognizes a neo-epitope in C9 that is expressed upon its incorporation into membrane C5b-9.

Similar results were obtained using cultured umbilical cells.

Figure 2A:
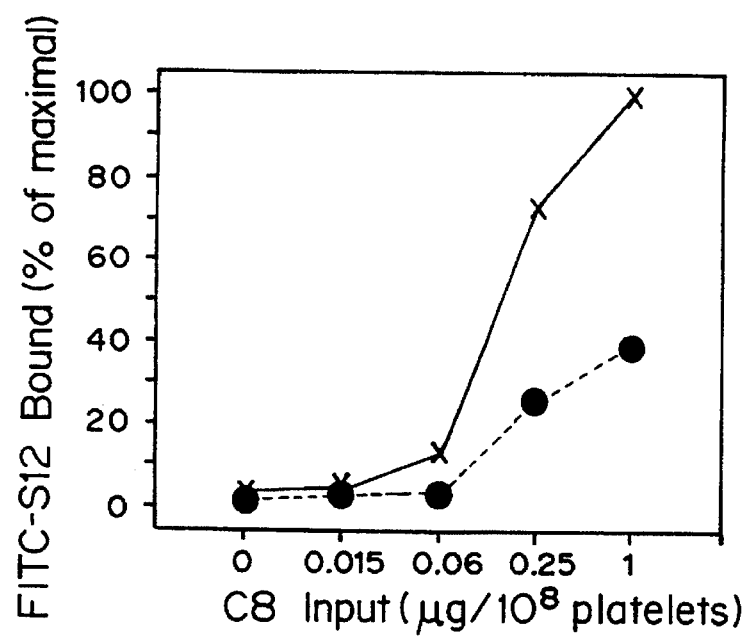
FIGS. 2A and 2B show the effect of α-P18 on C5b-9induced α-and dense granule secretion. Platelet α- (FIG. 2A) and dense (FIG. 2B) granule material secretion was measured after incubation of platelets with either 0 µg α-P18/ml (-●--●-) or 100 µg α-P18/ml (-X--X-) in the presence of various concentrations of C8 (0, 0.015, 0.06, 0.25, and 1 µg C8/$10^8$ platelets). The release of LDH is also shown by (Δ) for release in the absence of α-P18 and by (□) in the presence of α-P18.

Effect of α-P18 on C5b-9 Induced Secretion and Activation of Cell Surface GPIIb-IIIa The increased amount of activated C9 detected on the surface of platelets exposed to α-P18 suggested that this antibody might also affect the susceptibility of these cells to the stimulatory or cytolytic effects of the C5b-9 proteins. As shown in FIGS. 2 and 3, incubation with α-P18 markedly potentiated the capacity of the C5b-9 proteins to induce secretion from both α- and dense granules, but caused little increase in the platelet's susceptibility to lysis by these complement proteins.

α-Granule secretion (FIG. 2A) was monitored by the total binding of monoclonal antibody FITC-S12. Dense granule secretion (FIG. 2B) of the same samples was monitored by the release of $^{14}$C-serotonin. Cells were exposed to eisner 0 or 100 µg/ml α-P18 (Fab) before C5b-9 assembly. Also shown is LDH release under these conditions: 0 µg/ml α-P18; 100 µg/ml α-P18. Data for complement-free controls (0 vs. 100 µg/ml α-P18): α-granule secretion, 2.2% vs. 2.8%; dense granule secretion, 3.7% vs. 3.6%; LDH release, 1.0% vs. 1.0%.

Figure 3A:
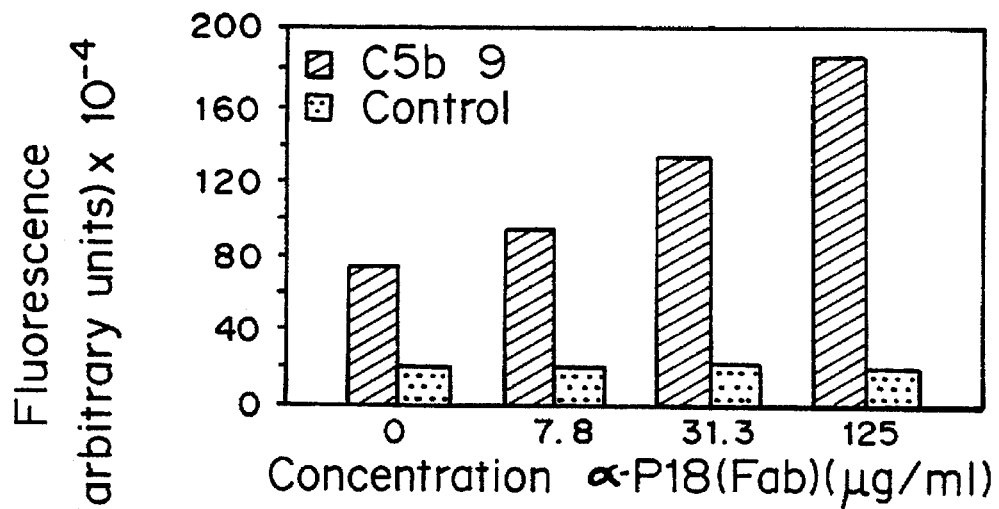
FIGS. 3A, 3B, and 3C show the platelet response as a function of α-P18 Fab concentration, 0, 7.8, 31.3, and 125 µg α-P18/ml: α-granule secretion as measured by FITC-S12 binding (FIG. 3A), GPIb-containing microparticles formation (FIG. 3B), and coagulation factor Va binding site exposure as measured by FITC-V237 binding (FIG. 3C). Solid bars denote α-P18 treated platelets and hatched bars denote control C5b-9 platelets.
Figure 3B:
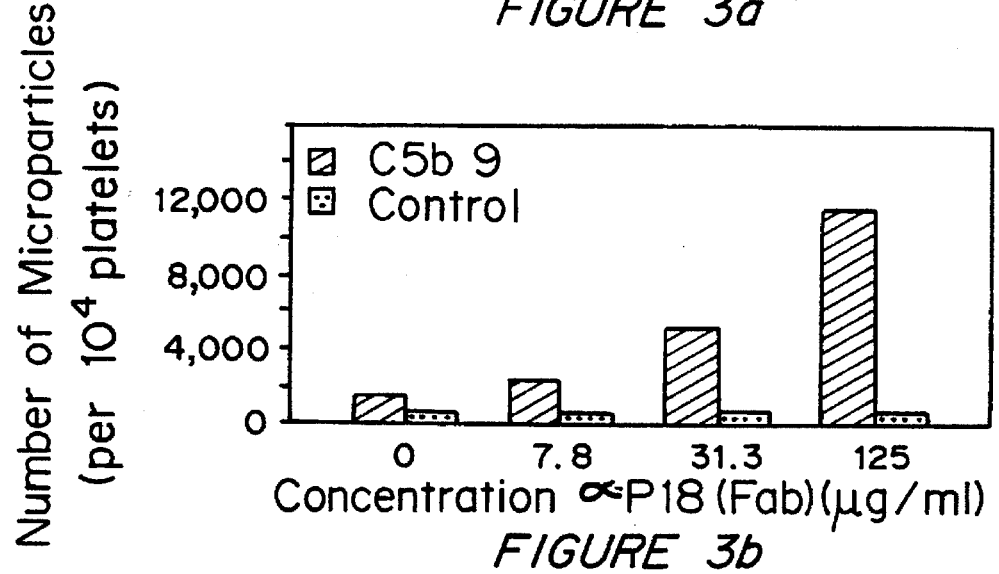
Figure 3C:
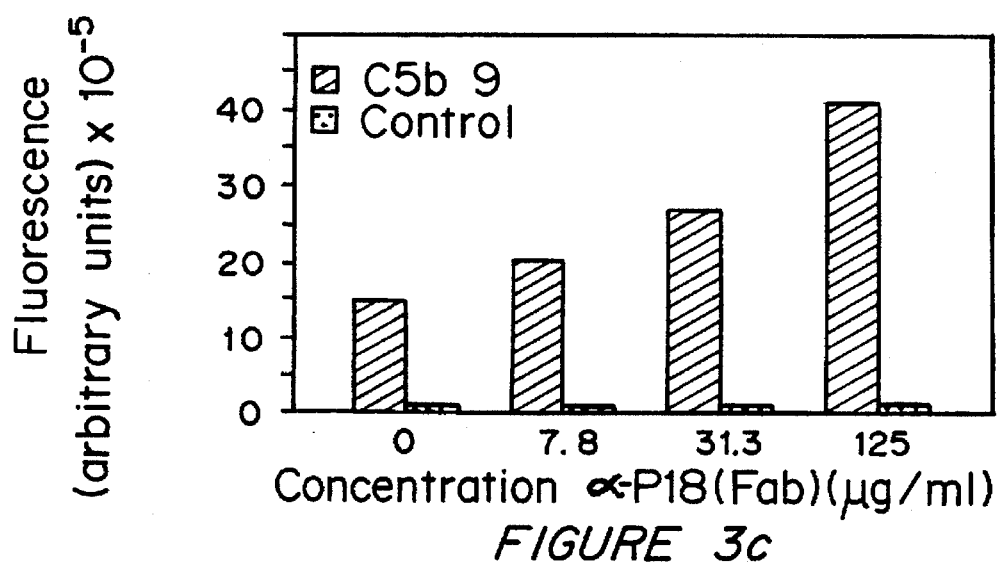

C5b67 platelets were incubated for 15 min at 23° C. with α-P18 (Fab; concentrations given on abscissa) before addition of C8 (1 µg per $10^8$ platelets) plus C9 (4 µg per $10^8$ platelets). After additional incubation for 10 min at 37° C., samples were processed for flow cytometry. FIG. 3A shows α-granule secretion measured by FITC-S12 binding. FIG. 3B shows formation of GPIb-containing microparticles. FIG. 3C shows the exposure of factor Va binding sites measured by FITC-V237 binding. In each panel, hatched bars denote data for C5b-9 platelets and solid bars denote data for C5b67 controls exposed to the identical concentrations of α-P18.

As demonstrated by FIG. 3A, this potentiation of C5b-9 stimulated secretion of platelet storage granules increased in a dose-dependent fashion with the concentration of the antibody. At these concentrations, α-P18 alone, or in combination with C5b-8, in the absence of added C9, did not directly stimulate platelet secretion nor did this antibody potentiate the platelet's secretory response to stimulation by low dose thrombin or phorbol ester.

Figure 4:
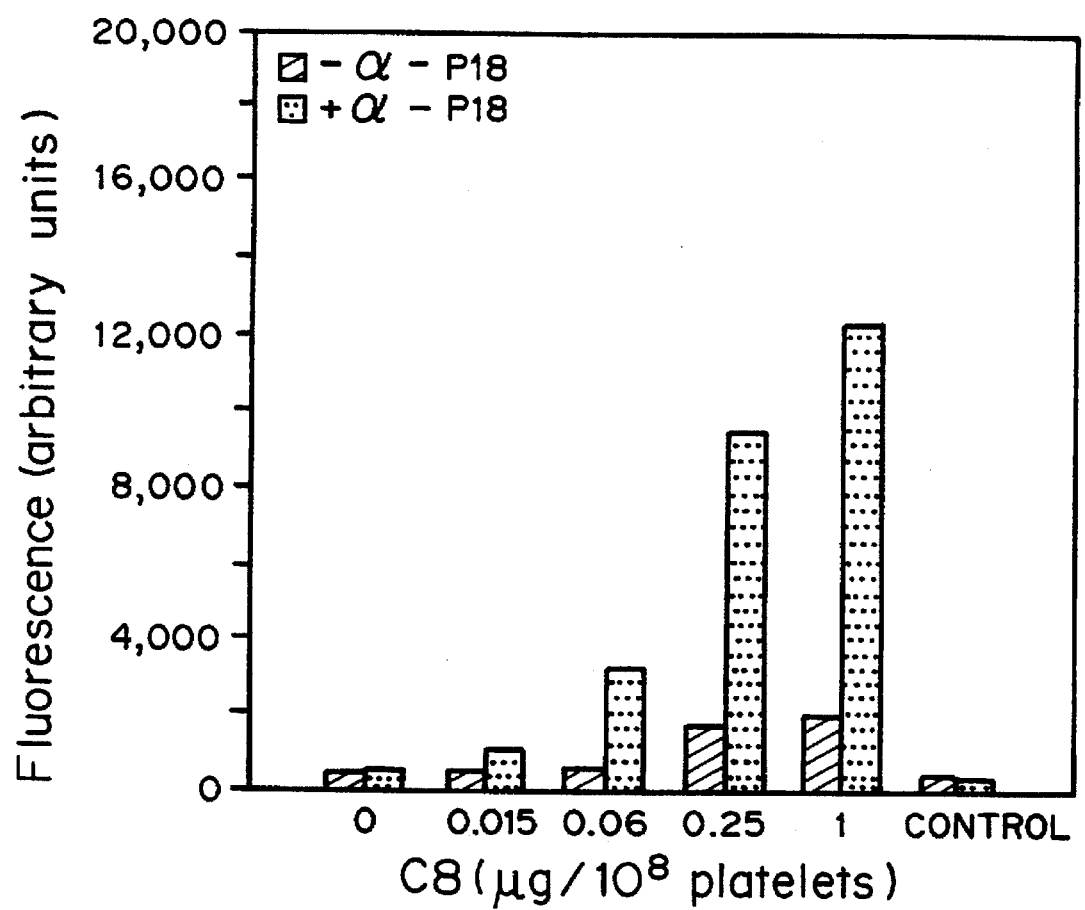
FIG. 4 shows the effect of α-P18 on C5b-9-induced expression of the PAC1 epitope in cell surface GPIIb-IIIa, as a function of C8 concentration, 0, 0.015, 0.06, 0.25, and 1 µg C8/$10^8$ platelets. Hatched bars denote FITC-labeled anti-GPIIb-IIIa antibody binding to control C5b-9 platelets and solid bars denote FITC-labeled anti-GPIIb-IIIa antibody binding to platelets pretreated with 100 µg/ml α-P18.

In addition to potentiating the platelet's secretory response to C5b-9, α-P18 also caused a marked increase in the C5b-9-dependent binding of monoclonal antibody FITC-PAC1 to the platelet surface as shown in FIG. 4. The PAC1 monoclonal antibody recognizes a conformational neo-epitope expressed by activated cell surface GP IIb-IIIa (the platelet's fibrinogen receptor).

C5b-9 assembly and incubation with α-P18 was performed as described for the data shown in FIG. 1, and conformational activation of membrane GPIIb-IIIa complexes probed by staining with FITC-PAC1. Hatched bars denote data for C5b-9 platelets (no α-P18); solid bars denote data for the same platelets pre-treated with 100 μg/ml α-P18 (Fab) before C8 and C9 additions. Controls refer to complement-free platelets.

Effect of α-P18 on the Procoagulant Activity of the C5b-9 Proteins

In addition to stimulating platelet and endothelial cell secretion, the C5b-9 proteins have been shown to initiate the release of small membrane vesicles, approximately 100 nM diameter, also known as platelet factor 3, from the cell surface that incorporate plasma membrane glycoproteins Ib, IIb, and IIIa, and the α-granule membrane derived glycoprotein GMP-140. The release of these membrane microparticles from the platelet surface is directly coupled to the influx of $Ca^{2+}$ into the platelet cytosol, and results in exposure of membrane receptors for factor Va and expression of catalytic surface for the prothrombinase enzyme complex. As illustrated by FIG. 3B and flow cytometry showing the effect of α-P18 on the release of membrane microparticles from platelets exposed to C5b-9, prior treatment with α-P18 greatly increased the number of microparticles released the platelet surface upon C9 binding to membrane C5b-8. In these studies, platelets and their derived membrane microparticles were quantitated using biotin-AP1, as described by Sims, et al., *J. Biol. Chem.* (1988).

C5b67 platelets were incubated with either 0 or 100 μg/ml α-P18 (Fab) before addition of C8 and C9. After incubation for 10 min at 37° C., the cells were stained with monoclonal antibody AP1 (directed against GP Ib) and analyzed by flow cytometry. The red fluorescence threshold was set so that only GP Ib-positive particles were analyzed. Data for complement-free controls exposed to 0 or 100 μg/ml α-P18 was obtained for purposes of comparison. In these studies, the number of microparticles detected (as percent of all GP-Ib-positive particles analyzed) was 9.7% and 9.2% for the controls, respectively, and 29% and 74% with antibody.

α-P18 alone did not induce vesiculation of the platelet surface nor did this antibody increase the number of microparticles detected when platelets were exposed to other agonists. The distribution of cell surface components between platelets and the shed microparticles is summarized in Table II.

TABLE II

Effect of α-P18 on Microparticle Formation[1]

| | | # | FITC-MAC Bound | | FITC-V237 Bound | |
|---|---|---|---|---|---|---|
| | α-P18[2] | Micro-particles[3] | Platelets | Micro-particles | Platelets | Micro-particles |
| C5b-9[4] | + | 24,560 | 149,500 | 171,400 | 1,651,600 | 4,396,500 |
| | − | 1,810 | 58,500 | 19,700 | 877,000 | 610,400 |
| C5b-8 | + | 790 | 0 | 0 | 160,000 | 35,900 |
| C5b67 | − | 790 | 0 | 0 | 166,900 | 28,300 |
| | + | 790 | 0 | 0 | 149,900 | 30,900 |
| | − | 790 | 9 | 4 | 159,200 | 30,700 |
| Control | + | 770 | 0 | 0 | 171,500 | 28,100 |
| | − | 760 | — | — | 174,900 | 27,300 |

Footnotes:
[1]Distribution of FITC-labeled antibodies between platelets and platelet-derived microparticles as discriminated by light scattering gates. Data expressed as total fluorescence in each gate (arbitrary fluorescence units). All data corrected for autofluorescence and non-specific binding of labeled antibody.
[2]Platelets incubated in presence (+) or absence (−) of 100 μg/ml α-P18 (Fab).
[3]Number of microparticles detected per $10^4$ platelets.
[4]C5b-9 (and intermediates) assembled as described in Materials and Methods, using 1 μg C8 per $10^8$ platelets per ml.

Inspection of these data reveals that the increase in membrane-incorporated C9 due to α-P18 (plotted in FIG. 1) is largely accounted for by C5b-9 complexes bound to GP Ib-positive microparticles. Since all membrane C5b-8 is initially on the platelet surface (the vesiculation of microparticles from the plasma membrane initiated only after C9 binds to its receptor, membrane C5b-8), these data suggest that the α-P18 mediated increase in plasma membrane-inserted C9 is ultimately compensated by the triggered vesiculation of assembled C5b-9 complexes from the platelet surface.

Figure 5A:
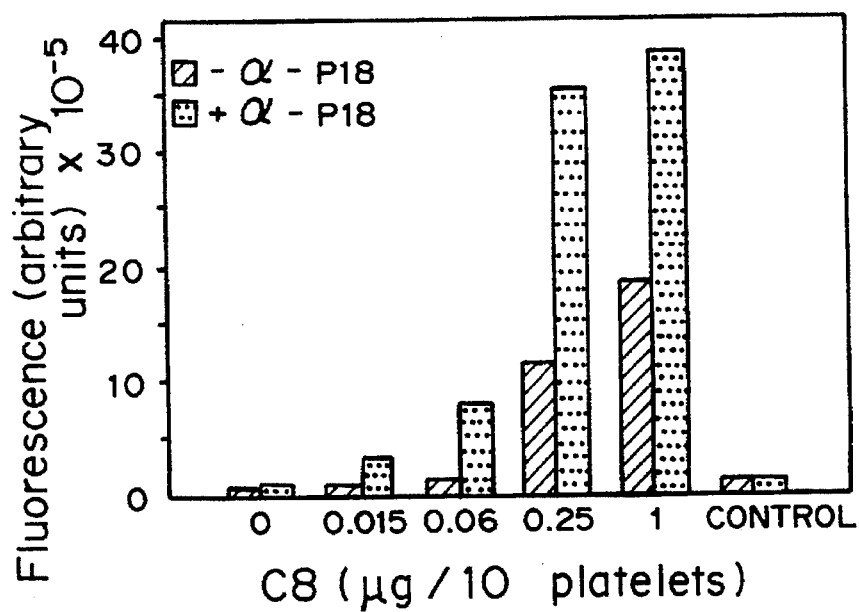
FIGS. 5A and 5B show the effect of α-P18 on expression of platelet procoagulant activity, as a function of C8 concentration, 0, 0.015, 0.06, 0.25, and 1 µg C8/$10^8$ platelets.

In addition to increasing C9 incorporation and microparticle formation, α-P18 caused a 4-to-5-fold increase in the number of factor Va binding sites exposed upon C5b-9 binding to the platelet surface, as shown by FIGS. 3C and 5A. This increase in total factor Va binding sites represented a 7-fold increase due to new sites exposed on microparticles that were released from the surface of a α-P18 treated platelets, combined with a two-fold increase in the number of factor Va binding sites exposed on the cells themselves under these conditions, as shown by Table II. This increased exposure of factor Va binding sites due to the presence of α-P18 resulted in a comparable increase in the C5b-9-induced expression of catalytic membrane surface for the prothrombinase enzyme complex.

Figure 5B:
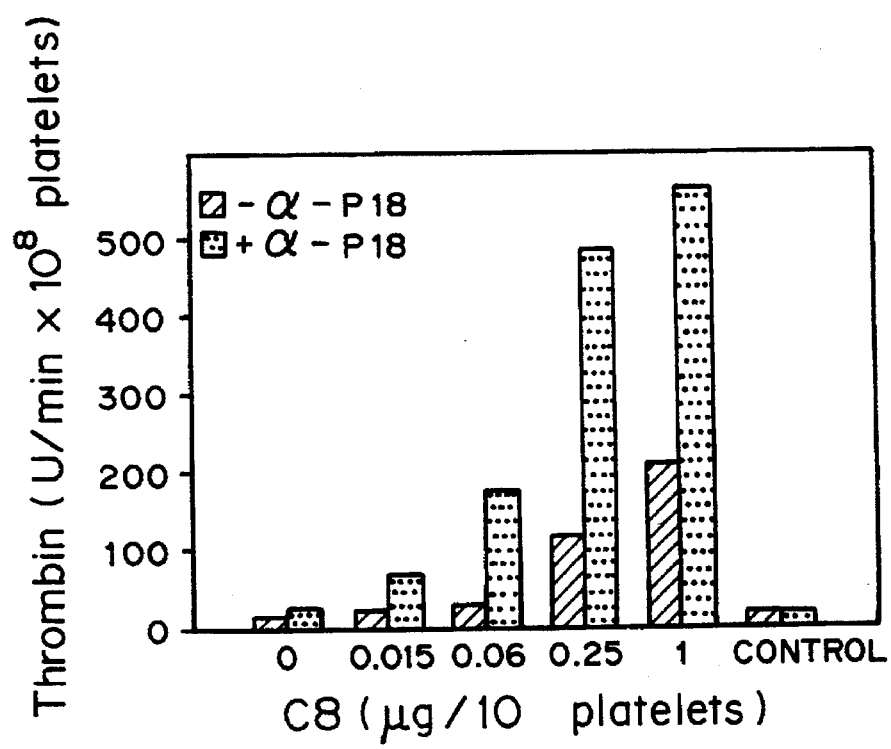

Platelets were incubated with α-P18 and the C5b-9 proteins under conditions described for the data shown in FIG. 1, and then analyzed for exposure of membrane sites for the prothrombinase enzyme complex, as shown in FIG. 5A. Factor Va binding sites were measured using a monoclonal antibody against factor Va light chain (FITC-V237), measured in the presence of 2 μg/ml of the ligand, with the data representing total membrane sites for factor Va (platelet and microparticle-associated). FIG. 5B shows prothrombinase activity measured as described in Materials and Methods. Concentrations of α-P18 (Fab) were either 0 or 100 μg/ml. Data for complement-free controls are also shown.

In summary, these data suggest that the platelet and endothelial cell plasma membrane contain an inhibitor of the terminal complement C5b-9 proteins that shares both functional and antigenic properties with the 18 kDa protein recently identified in the human erythrocyte membrane. In erythrocytes, this protein appears to serve a key role in restricting the cytolytic consequence of C5b-9 assembly. In addition to contributing to the normal resistance of human platelets and endothelial cells to lysis by complement, this membrane component appears to directly attenuate the capacity of the C5b-9 proteins to induce procoagulant responses and platelet and leukocyte adhesive endothelial responses.

In platelets exposed to α-P18, the half-maximal concentration of C8 required for C5b-9-induced secretion (FIG. 2), exposure of the PAC1 epitope in GPIIb-IIIa (FIG. 4), exposure of factor Va binding sites (FIG. 5A) and the expression of prothrombinase activity (FIG. 5B) decreased by more than 10-fold. This was accompanied by increased binding of activated C9 at each input of C8 (to Pre-assembled plasma membrane C5b67; FIG. 1).

Taken together, these data suggest that epitopes recognized by α-P18 include functional domains of a membrane component that inhibits formation of the C5b-9 complement pore, specifically by interfering with the binding and/or activation of C9 by membrane bound C5b-8. Similar results have been obtained in studies with erythrocytes and endothelial cells. The requirement for activated C9 (incorporated into membrane C5b-9 complexes) in the platelet responses observed in the presence of this antibody is underscored by the failure to detect significant platelet activation when either C8 alone (in the absence of C9) was added to C5b67 platelets exposed to α-P18 (Table II), or, when saturating amounts of C9 were added to these platelets in the absence of added C8 (FIGS. 2,4,5).

In addition to confirming that the effect of α-P18 is on the capacity of the platelet and endothelial cell plasma membrane to regulate assembly of the C5b-9 pore (and not directly on the stimulatory state of the cell per se), these data exclude the possibility that the increased activation of the complement pore observed in the presence of this antibody arose from trace contamination of the IgG (Feb) by either rabbit C8 or C9.

Figure 2B:
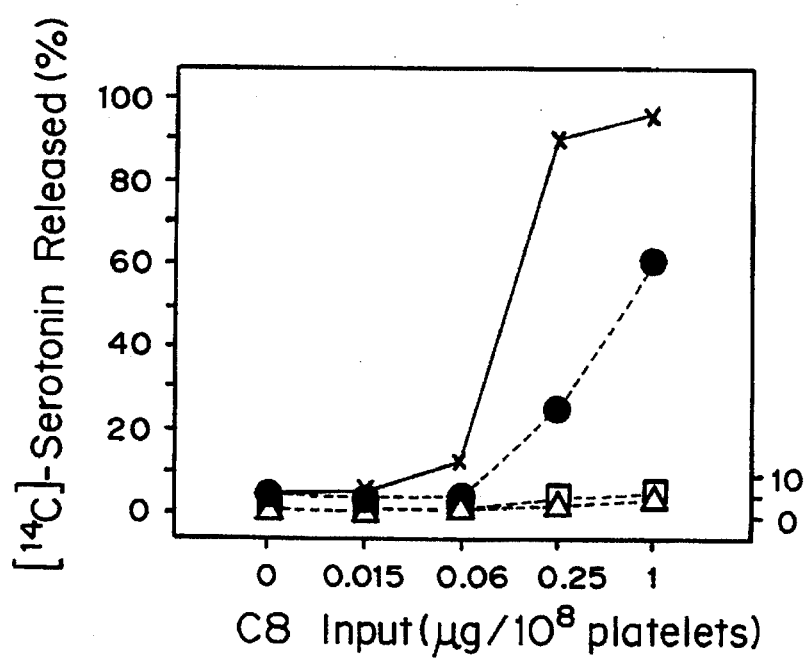

As shown in FIG. 2B, pre-treatment with α-P18 did slightly increase the lysis of platelets exposed to C5b-9 (as measured by release of LDH). Nevertheless, this effect on the platelet's susceptibility to cytolysis by C5b-9 was quite small, and total cell lysis never exceeded 5% under the experimental conditions. This stands in contrast to the marked effect of this antibody on the sensitivity of platelets to the cell-stimulatory effects of the C5b-9 proteins. Most notably, α-P18 greatly increased both the number of membrane microparticles shed from the surface of C5b-9 treated platelets and the number of factor Va binding sites exposed on these membrane surfaces (microparticle and platelet). This capacity of the platelet to shed cell surface components is integrally related both to the observed inactivation of functional C5b-9 pores, which restores the electrochemical integrity of the plasma membrane, as well as to the exposure of membrane receptors for factor Va, which initiates the prothrombinase reaction.

The capacity of this blocking antibody to potentiate the C5b-9-induced exposure of factor Va binding sites, and thereby increase prothrombinase activity, suggests that a deletion or inactivation of the membrane epitopes recognized by this antibody would also potentiate the procoagulant response of platelets exposed to low levels of complement activation.

It is apparent from the above findings that inactivation of functional C5b-9 inhibitor or a reduction in the platelet or endothelial cell membrane concentration of C5b-9 inhibitor molecules would result in increased platelet or endothelial cell activation. Conversely, administration of this inhibitor, or a polypeptide representing its functional domain and possessing C5b-9 inhibitory activity, to block platelet or endothelial cell activation in a patient in need of such treatment, would thereby protect the patient from C5b-9 mediated procoagulant and prothrombotic responses.

In this context, it is important to note that affected red cells obtained from patients with the acquired stem cell disorder Paroxysmal Nocturnal Hemoglobinuria (PNH) have been shown to exhibit abnormal sensitivity to lysis by the C5b-9 proteins. This has been attributed to the deletion of homologous restriction factor. Platelets obtained from patients with PNH have been shown to be abnormally sensitive to fluid phase complement activation, and this disorder is characterized by an unusually high risk of venous thrombosis. The data with α-P18 suggest a possible mechanism by which loss of the C5b-9 inhibitory activity from the platelet plasma membrane would directly give rise to the thrombotic episodes that are associated with this disorder. This same finding is equally applicable to other types of complement mediated disorders, particularly in view of the discovery that the inhibitor is also found on the surface of endothelial cells. As a result, administration of the inhibitor protein, whether purified from cells or expressed from cells engineered using recombinant techniques, or portions of the peptide having the same measurable activity, can be administered to these patients to alleviate the severity of the disorder.

Treatment of patients with immune disorders and diseases such as immunovasculitis, rheumatoid arthritis, scleroderma, disseminated intravascular coagulation, lupus, paroxysmal nocturnal hemoglobinuria, thrombotic thrombolytic purpura, vascular occlusion, reocclusion after surgery, coronary thrombosis, and myccardial infarction, is accomplished by administering an effective amount of a composition containing a C5b-9 inactivator as defined above such that procoagulant processes are suppressed. In the case of transfused blood cells or transplanted organs or tissue, the purified membrane inhibitor of C5b-9, or the functionally equivalent polypeptide or antibody, is first coated on the cell surface before transplantation or transfusion into the recipient. The amount of composition that must be administered to a patient in need of such treatment will vary depending on the particular disorder or disease and the severity of affliction. Treatment dosages will also vary with the individual patient depending upon response to treatment, genetic variability, and effect of co-administered drugs. In general, however, the compositions disclosed herein are administered intravenously at a dosage of approximately nanograms of inhibitory protein or peptide per milliliter. Treatment can take the form of a single administration of the composition or can be administered periodically or continuously over an extended period of time, as required.

For treatment of immune disorder or disease, the C5b-9 inactivator is administered intravenously in a pharmaceutically acceptable carrier such as saline or a physiologically acceptable buffer.

Isolated, functionally active polypeptides able to inhibit C5b-9 also have utility for increasing the hemostatic efficacy and extending the in vitro storage time of blood and platelet preparations. There exists a great need for prolonging the half-life, and therapeutic efficacy of platelets stored in vitro. Platelet-containing solutions, particularly platelet-rich plasma (PRP), are in tremendous demand medically for transfusions. The current shelf life of platelet preparations is approximately 72 hours. An increase in the useful lifetime of such preparations represents a significant advancement in the state of the art and answers a pressing human and medical need.

In the case of human organs and tissue for transplantation, the C5b-9 inactivators would be added to the perfusate or storage medium to protect the vascular lining cells from ongoing complement activation during in vitro storage. Additionally, by coating these endothelial cells with a membrane-anchored C5b-9 inactivator, the organ or tissue would be protected from the cytolytic and thrombotic effects arising from complement activation initiated upon transplantation, thereby circumventing complement mediated acute rejection.

In the preferred embodiment, the C5b-9 inactivator is in combination with anticoagulant, such as ACD, CPD, heparin, or oxalate, such that the concentration in the platelets or PRP is approximately nanograms inactivator/ml. Similarly, for organ storage, the C5b-9 inactivator is in combination with perfusate or storage solutions, or culture medium, such that the concentration is approximately nanograms inactivator/ml.

It is apparent from the foregoing discussion that addition of polypeptides which act to inhibit the activity of C5b-9 towards human platelets and endothelium would reduce the incidence of C5b-9 mediated procoagulant and prothrombotic responses. Release of platelet granule enzymes and factors result in clotting of platelets and general deterioration of the platelet preparation, limiting the shelf life of such preparations. Thus, the addition of the disclosed compositions containing C5b-9 inhibitory polypeptides to platelet preparations will suppress the spontaneous initiation of a procoagulant state and increase the usable life of such preparations.

Compositions useful for extending the shelf life of platelet preparations stored in vitro contain C5b-9 inhibitor in an amount sufficient to inhibit C5b-9 mediated platelet activation. Generally, these compositions will be added to platelet preparations, such as platelet-rich plasma, such that the final concentration of inhibitory polypeptide in the preparation is in the range of greater than 2 Ki of the inactivator in the solution. For the 18 kDa protein and other polypeptides which incorporate a membrane binding domain, the therapeutically effective dosage will be less than 1 μg inactivator/ml. Useful composition may also contain additional anticoagulant agents such as oxalate, citrate, and heparin. The C5b-9 inhibitor containing compositions can be added to whole blood as it is collected or to platelet preparations after processing of the blood into isolated platelet concentrates.

Fluorescence-gated flow cytometry and monoclonal antibodies specific for selected plasma proteins (activated complement proteins and coagulation factors) and for activated cell surface markers (GPIIb-IIIa, GMP140) can be used to monitor the accumulation of cells surface C5b-9, exposure of membrane receptors for coagulation factors fVa and fXa, activation of platelet secretion and platelet fibrinogen receptors, and the release of plasma membrane derived platelet microparticles during in vitro cell storage. These methods can also be used to monitor the secretion or removal of C5b-9 inhibitory proteins from the platelet or endothelial cell surface. Additionally, the fluorescent membrane potentiometric dyes, such as the carbocyanine dyes, for example, diS-C3-5, can be used to measure transmembrane electrochemical gradients indicative of cell viability and metabolic integrity. Use of both of these methods in blood banking will greatly decrease waste as well as therapeutic efficacy of the platelets which are determined not to be activated.

Modifications and variations of the present invention will become obvious to one skilled in the art in view of the description. These modifications and variation are intended to fall within the scope of the appended claims.

We claim:

1. A method for inhibiting platelet or endothelial cell activation by complement proteins comprising:

administering to platelets and/or endothelial cells in an amount effective to inhibit platelet or endothelial cell activation a pharmaceutically acceptable composition comprising a monoclonal antibody which specifically binds to a component forming the C5b-9 complex and which inhibits the platelet or endothelial cell activating function of the C5b-9 complex wherein the platelet or endothelial cell activating function of the C5b-9 complex is characterized by initiation of a transient and reversible depolarization of the plasma membrane potential, a rise in cytosolic calcium, metabolic conversion of arachidonate to thromboxane to prostacyclin and activation of intracellular protein kinases; wherein activation of platelets is additionally characterized by shape changes, secretory fusion of intracellular storage granules with plasma membranes and the vesiculation of membrane components from platelet surfaces; and wherein activation of endothelial cells is additionally characterized by secretion of high molecular weight multimers of the platelet adhesion protein, yon Willibrand Factor, and translocation of GMP140 to the endothelial cell surface, and a pharmaceutically acceptable carrier.

2. The method of claim 1 wherein an effective amount of said monoclonal antibody is administered to a patient in need of treatment for a disease selected from the group consisting of disseminated intravascular coagulation, lupus, rheumatoid arthritis, scleroderma, paroxysmal nocturnal hemoglobinuria, thrombotic thrombolytic purpura, vascular occlusion, reocclusion, coronary thrombosis, myocardial infarction, and complement mediated inflammatory vascular disorders.

3. The method of claim 1, wherein the monoclonal antibody is a Fab fragment.

4. A composition for intravenous injection into a patient comprising:

an effective amount to inhibit platelet or endothelial cell activation of a monoclonal antibody which specifically binds to a component forming the C5b-9 complex and which inhibits the platelet or endothelial cell activating function of the C5b-9 complex wherein the platelet or endothelial cell activating function of the C5b-9 complex is characterized by initiation of a transient and reversible depolarization of the plasma membrane potential, a rise in cytosolic calcium, metabolic conversion of arachidonate to thromboxane to prostacyclin and activation of intracellular protein kinases; wherein activation of platelets is additionally characterized by shape changes, secretory fusion of intracellular storage granules with plasma membranes and the vesiculation of membrane components from platelet surfaces; and wherein activation of endothelial cells is additionally characterized by secretion of high molecular weight multimers of the platelet adhesion protein, yon Willibrand Factor, and translocation of GMP140 to the endothelial cell surface, and a pharmaceutically acceptable carrier.

5. The composition of claim 4 wherein the monoclonal antibody is a Fab fragment.

* * * * *

UNITED STATES PATENT AND TRADEMARK OFFICE
CERTIFICATE OF CORRECTION

PATENT NO. : 5,635,178
APPLICATION NO. : 08/207841
DATED : June 3, 1997
INVENTOR(S) : Peter J. Sims and Therese Wiedmer It is certified that error appears in the above-identified patent and that said Letters Patent is hereby corrected as shown below:

At column 1, lines 4 and 7, "C56-9" should be replaced with --C5b-9--; at column 1, lines 10 and 11, "The U.S. Government has rights in this invention by virtue of certain government grants." should be replaced with --The United States Government has rights in this invention by virtue of National Institutes of Health grant numbers HL36061 and HL36946.--

Signed and Sealed this

First Day of April, 2008

JON W. DUDAS
*Director of the United States Patent and Trademark Office*